(12) United States Patent
Fang

(10) Patent No.: US 9,328,074 B2
(45) Date of Patent: May 3, 2016

(54) PROCESS FOR PRODUCING ISOXAZOLINE DERIVATIVES

(71) Applicant: Guangyu Fang, Bristol (GB)

(72) Inventor: Guangyu Fang, Bristol (GB)

(73) Assignee: Guangyu Fawg, Bristol (GB)

( * ) Notice: Subject to any disclaimer, the term of this patent is extended or adjusted under 35 U.S.C. 154(b) by 0 days.

(21) Appl. No.: 14/473,720

(22) Filed: Aug. 29, 2014

(65) Prior Publication Data

US 2016/0060223 A1   Mar. 3, 2016

(51) Int. Cl.
*C07D 231/06*   (2006.01)

(52) U.S. Cl.
CPC .................................. *C07D 231/06* (2013.01)

(58) Field of Classification Search
CPC ..................................................... C07D 261/04
See application file for complete search history.

(56) References Cited

PUBLICATIONS

Charette, Helvetica Acta, vol. 85, 2002, p. 4468-4484.*

* cited by examiner

*Primary Examiner* — Michael Barker
*Assistant Examiner* — Karen Cheng

(57) ABSTRACT

A process for producing isoxazoline derivatives by ring-opening and cyclization of the corresponding cyclopropane derivatives with electrophilic nitrosylation reagents.

11 Claims, No Drawings

PROCESS FOR PRODUCING ISOXAZOLINE DERIVATIVES

FIELD OF THE INVENTION

The present invention relates to a highly efficient process for producing isoxazoline derivatives.

BACKGROUND OF THE INVENTION

Isoxazoline derivatives represented by the general formula (1)

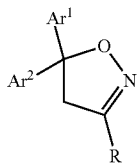
(1)

wherein $Ar^1$ represents an aryl group which may be substituted; $Ar^2$ represents another aryl group, which may be substituted as well, and may or may not be the same as $Ar^1$; R represents electron withdrawing group including but not limited to alkoxycarbonyl, aryloxycarbonyl, aminocarbonyl, cyano, alkylcarbonyl, arylcarbonyl, formyl, alkylsulfinyl, arylsulfinyl, alkylsulfonyl or arylsulfonyl are compounds that are widely used in the field of agriculture. One particular example of the isoxazoline derivatives is ethyl 5,5-diphenyl-3-isoxazolinecarboxylate (commercially known as isoxadifen-ethyl) which is used as a safener in a herbicide for corn production (WO 01/54501/A2 by Syngenta participations AG) and as an insecticide (WO 2006/8110 A1 by Bayer cropscience AG). The estimated worldwide annual consumption of isoxadifen-ethyl is 800 to 1000 tons.

Heretofore, the isoxazoline derivatives represented by the formula (1) are generally prepared through dipolar [2+3] cycloaddition of the corresponding alkenes represented by the general formula (2)

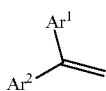
(2)

and 1-chloro-oxime represented by the general formula (3) (DE 4331448 A1 19950323)

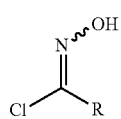
(3)

wherein $Ar^1$, $Ar^2$ and R are as defined above.

Another prior art process for preparing the isoxazoline derivatives represented by the formula (1) is the [2+3] dipolar cycloaddition of alkenes represented by the formula (2) with nitro compounds represented by the general formula (4) (Tetra. Asymmetry, 2008, 19, 2850-2855)

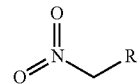
(4)

wherein R is as defined above.

These two processes to prepare the isoxazoline derivatives are generally well-known in the prior art. However, the disadvantages of the processes are also generally recognized in the field, particularly for preparing ethyl 5,5-diphenyl-3-isoxazolinecarboxylate:

A) Both of these two processes are low efficiency: through these processes the isoxazoline derivative is produced in modest yield (86% yield using one equivalent of ethyl 2-chloro-2-hydroxyiminoacetate and 1.5 equivalents of 1,1-diphenylethene (DE 4331448 A1 19950323), and 75% yield when the nitro compound used (Tetra. Asymmetry, 2008, 19, 2850-2855).

B) The materials used in these processes are expensive because they have to be made in two or three steps from more common materials; for example, the alkenes, 1,1-diphenylethene represented by the general formula (2), wherein $Ar^1$, $Ar^2$ are phenyls, is commonly made by the reaction of the corresponding diphenyl ketone and the Grignard reagent in an anhydrous pyrophoric ethereal solvent, followed by dehydration with strong acid; and the ethyl 2-chloro-2-hydroxyiminoacetate represented by the general formula (3), wherein R is ethoxycarbonyl, is generally prepared from glycine via esterification with large excess of thionyl chloride, a process through which a large quality of hydrogen chloride and sulphur dioxide are released; followed by oxidation with nitrite under acidic conditions, and the ethyl 2-chloro-2-hydroxyiminoacetate was obtained in only 55-76% overall yield (Bulletin of the Chemical Society of Japan, 1971, 44, 219); and the synthesis of the nitro compounds (4) is achieved in 60-78% yield through nitration of ethyl acetoacetate with fumic nitric acid in acetic anhydride (U.S. Pat. No. 5,162,572 A1 1992). Overall, the existing processes for producing the isoxazoline derivatives represented by the general formula (1) are of low efficiency, highly expensive, and environmentally costly. As a result, there is real need for a novel cost-effective process to improve the production yield and ease the environmental concern.

Cyclopropane derivatives with vicinal electron donor and acceptor substituents are able to be subjected to heterolytic ring cleavage to form 1,3 zwitterionic intermediates (Reissig, H.-U. Topics of Current Chemistry, 144, 73, 1988). In particular, when treated with unsaturated electrophiles they undergo [2+3] type reactions to form five membered carbon or heterocyclic compounds (Shimada, S.; Hashimoto, Y.; Sudo, A.; Hasegawa, M.; Saigo, K. Journal of Organic Chemistry, 57, 7126, 1992; Graziano, M. L.; Isece, M. R.; Cermola, F. Journal of Chemical Research, (S) 82, (M) 0622, 1996). Among these unsaturated electrophiles, nitrosylation reagents including NOCl, NOBr, $NOBF_4$, $NaNO_2$—$CF_3CO_2H$ have been reported to react with cyclopropane derivatives to form isoxazoline derivatives or/and isoxazodine derivatives: cyclopropane derivatives that have been reported to react with NOCl include ethyl 2,2-dimethoxycyclopropanyl carboxylate, ethyl 2,2-dimethoxy-3,3-dimethylcyclopropanyl carboxylate, ethyl 2-ethoxy-cyclopropanyl carboxylate, ethyl 2,2-dimethoxy-3-methylcyclopropanyl carboxylate (Cermola, F.; Gioia, L. D.; Graziano, M. L.; Isece, M. R.; Journal of Chemical Research 677-681, 2005); cyclopropane derivatives that have been reported to react with NOBF$_4$ include ethyl 2-ethoxy-cyclopropanyl carboxylate (Cermola, F.; Gioia, L. D.; Graziano, M. L.; Isece, M. R.; Journal of Chemical Research 677-681, 2005), 1,1-dichloro-2-arylcyclopropane (Lin, S.-T.; Kuo, S.-H.; Yang, F.-M. Journal of Organic Chemistry, 62, 5229, 1997), 1-aryl-2-arylcyclopropane (Mizuno, K.; Ichinose, N.; Tamai, T.; Otsuji, Y. Journal of Organic Chemistry, 57, 4669-4675, 1992), phenylcyclopropane (Kim, E. K.; Kochi, J. K. Journal of American Chemical Society, 113, 4962, 1991); cyclopropane derivatives that have been reported to react with NaNO$_2$—CF$_3$CO$_2$H include ethyl 2-arylcyclopropanyl carboxylate (Kadzhaeva, A. Z.; Trofimova, E. V.; Fedotov, A. N.; Potekhin, K. A.; Gazzaeva, R. A.; Mochalov, S. S.; Zefirov, N. S. Journal of Heterocyclic Compounds 45, 595, 2009). However, examples presented in these publications listed above clearly demonstrate that the reaction of nitrosylation reagents and cyclopropanes is not feasible as a method for preparing isoxazoline derivatives, as the reaction generally delivers a mixture composed of the desired isoxazoline derivatives, isoxazlidine derivatives and other non-cyclic compounds. And the desired isoxazoline derivatives were generated only in low yields.

This invention discloses a novel process to prepare isoxazoline derivatives represented by the general formula (1) in high efficiency from easy accessible materials. Therefore, it addresses the need for a more cost-effective and more environmentally friendly technology for the synthesis process. This need is solved by the subject matter disclosed herein.

SUMMARY OF THE INVENTION

This invention provides an efficient process to produce isoxazoline derivatives represented by the general formula (1)

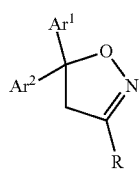

(1)

wherein Ar$^1$, Ar$^2$ represent aryl groups that may contain one to five substituents that include but not limited to halide, alkyloxy, alkyl, aryl, carbonyl, nitro, cyano; and Ar$^2$ may or may not be the same as Ar$^1$; R represents an electron withdrawing group including but not limited to alkoxylcarbonyl, aryloxylcarbonyl, aminocarbonyl, cyano, alkylcarbonyl, arylcarbonyl, formyl, alkylsulfinyl, arylsulfinyl, alkylsulfonyl, arylsulfonyl from the corresponding cyclopropane derivatives represented by the general formula (5)

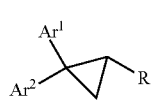

(5)

wherein Ar$^1$, Ar$^2$ and R are as defined above, with electrophilic nitrosylation reagents including but not limited to nitrosylchloride, nitrosylbromide, nitrosylsulfuric acid or a combination of sodium nitrite or potassium nitrite with strong acid including but not limited to sulphuric acid, trifluoroacetic acid, hydrogen chloride or nitric acid, or with Lewis acid including but not limited to BF$_3$, AlCl$_3$ in the solvent including but not limited to acetic acid, trifluoroacetic acid, sulphuric acid, halogenated solvent such as dicloromethane, 1,2-dichloroethane etc, aromatic solvent such as benzene, toluene, chlorobenzene etc; aliphatic ether, aliphatic ester, acetonitrile, at the temperature ranging from −20° C. to 100° C.

DETAILED DESCRIPTION OF THE INVENTION

Applicant has discovered an efficient process to prepare the isoxazoline derivatives represented in the general formula (1)

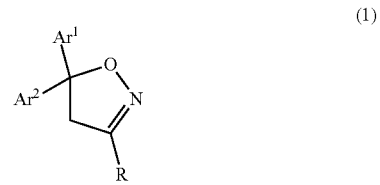

by reacting the cyclopropane derivatives represented in the general formula (5)

with an electrophilic nitrosylation reagent; wherein Ar$^1$, Ar$^2$ in both formula (1) and (5) represent aryl groups that may be substituted, and Ar$^2$ may or may not be the same as Ar$^1$; R represents electron withdrawing group including but not limited to alkoxylcarbonyl, aryloxylcarbonyl, aminocarbonyl, cyano, alkylcarbonyl, arylcarbonyl, formyl, alkylsulfinyl, arylsulfinyl, alkylsulfonyl, arylsulfonyl, nitro; and the electrophilic nitrosylation reagent include but not limited to nitrosylchloride, nitrosylbromide, nitrosylsulfuric acid and electrophilic nitrosylation reagents composed of at least one member of nitrites including but not limited to lithium nitrite, sodium nitrite or potassium nitrite and one member of strong acids including but not limited to sulphuric acid, trifluoroacetic acid, hydrogen chloride, nitric acid, or with Lewis acid including but not limited to BF$_3$, AlCl$_3$ in the solvent including but not limited to acetic acid, trifluoroacetic acid, sulphuric acid, halogenated solvent such as dicloromethane, 1,2-dichloroethane etc.; aromatic solvent such as benzene, toluene, chlorobenzene etc.; aliphatic ether, aliphatic ester, acetonitrile at the temperature ranging from −20° C. to 100° C.

The invention is described in details via preparation of ethyl 5,5-diphenyl-3-isoxazolinecarboxylate. The corresponding cyclopropane derivative, ethyl 2,2-diphenylcyclopropanylcarboxylate, is prepared via an amended known one step process: diphenyl diazomethane solution was efficient, economic and environmentally benign produced by oxidizing diphenylketone hydrazine with either yellow mercury oxide (Synlett, 11, 1623-1626, 2010; Yu, J.; Lian, G.; Zhang, D. Synthetic communications, 37, 37-46, 2007), manganese dioxide (Tetrahedron, 54, 6867-6896, 1998) or sodium hypochlorite (Tokushima, I.-K.; Naruto, I.-W.; Tokushima, M.-S. PCT/JP94/02124); and decomposition of diphenyl diazomethane in the presence of ethyl acrylate at 50° C. produce ethyl 2,2-diphenylcyclopropylcarboxylate in great than 94% overall yield. The ethyl 2,2-diphenylcyclopropanylcarboxylate thus prepared is normally contaminated with less than five percent of various impurities depending on the exact method used. The presence of impurities in the cyclopropane derivatives obtained does not have significant impact on the production of the isoxazoline derivatives.

Non-limiting examples of electrophilic nitrosylation reagent used in the reaction of this invention include nitrosylchloride, nitrosylbromide, nitrosylsulfuric acid or a combination of nitrite salt including but not limited to sodium nitrite or potassium nitrite with strong acid including but not limited to sulphuric acid, trifluoroacetic acid, hydrogen chloride, nitric acid, or with strong Lewis acid including but not limited to boron trifloride, aluminium trichloride. Non-limiting examples of solvent used in the reaction of this invention include acetic acid, trifluoroacetic acid, sulphuric acid, nitric acid, halogenated solvent such as dicloromethane, 1,2-dichloroethane; aromatic solvent such as benzene, toluene, chlorobenzene; aliphatic ether, aliphatic ester, acetonitrile.

The mole ratio of nitrosylation reagent to the cyclopropane derivatives represented by the general formula (5) varies from 1:1 to 10:1. And the most preferred ratio is approximately 1.1:1.

The concentration of the cyclopropane derivatives represented by the general formula (5) used in the reaction can range from 0.01 mole per liter to 10.0 mole per liter, the preferable concentration is within the range of 0.1 mole per liter to 5.0 mole per liter.

In this invention, the reaction is a strong exothermic process. It is preferable to maintain the reactants at the temperature as low as possible while slowly mixing the nitrosylation reagent mentioned above with the cyclopropane derivatives represented by the general formula (5). Generally the reaction temperature needs to be maintained below 100° C., and more preferred below 40° C.

The Examples listed below illustrate methods for preparing the isoxazoline derivatives according to the invention.

EXAMPLES

Example 1

Synthesis of 2,2-diphenylcyclopropanyl carboxylate ethyl ester

Diphenylketone hydrazone (3.92 g, 20 mmol) was mixed with yellow mercury oxide (4.33 g, 20 mmol) in 40 mL petroleum. The mixture was stirred at the temperature less than 20° C. for 16 hours. The deep red solution of diphenyl diazomethane in petroleum was added into ethyl acrylate (6.0 g, 60 mmol) at 50° C. in ten minutes. When the red colour fade off the solvent and excess of ethyl acrylate were removed under reduced pressure and the crude product obtained was further purified over silica chromatography to furnish 2,2-diphenylcyclopropanyl carboxylate ethyl ester 5.11 g (96% yield) as a pale yellow oil. $^1$H NMR (400 MHz, CDCl$_3$): 7.36-7.17 (10H, m), 4.00-3.83 (2H, m), 2.54 (1H, dd, J=8.3, 6.0 Hz), 2.17 (1H, dd, J=1H, dd, 6.0, 4.8 Hz), 1.59 (1H, dd, J=8.3, 4.8 Hz), 1.01 (3H, t, J=7.1 Hz).

Example 2

Synthesis of 2,2-diphenylcyclopropanyl carboxylate ethyl ester

Diphenylketone hydrazone (8.9 g, 45.4 mmol) in DCM (19 mL) was mixed with KI (0.45 g) in water (0.6 mL) and benzyldimethyloctylammonium chloride (10 mg). To the mixture was added the aqueous solution composing of 25% NaOH (27 mL), water (18 mL), and sodium chlorite (12-14%, 28 mL) at 5° C. with vigorous stirring. Twenty minutes later after addition, the stirring was turned off to let the reaction mixture separate. The red DCM solution was separated and dried over anhydrous Na$_2$SO$_4$. After removing the desiccant, the solvent was removed under reduced pressure; the residue was re-dissolved in hexane, and the unreacted hydrazone and side product was insoluble in hexane and removed by filtration. The red hexane diphenyl diazomethane solution was added to ethyl acrylate (13.6 g, 136 mmol) at 50° C. within 30 mints. When the red colour fade off the solvent and excess of ethyl acrylate was removed under reduced pressure to give crude product with 94% purity in 56-94% yield.

Experiment 3

Synthesis of 2,2-diphenylcyclopropanyl carboxylate ethyl ester

To the solution of diphenylketone hydrazone (45 g, 0.227 mol) in 220 mL chloroform was added activated MnO$_2$ (Aldrich, 85%, 49.4 g, 0.567 mol). The mixture was vigorously stirred at the temperature less than 20° C. until all starting material had been consumed. The solid was removed by filtration over celite. And the deep red solution was added to 68 g ethyl acrylate at 50° C. in 40 mins. When the red colour fade off, the chloroform (more than 200 mL) and excess ethyl acrylate (37 g) were collected by distillation; and the crude product obtained containing great than 96% of 2,2-diphenylcyclopropanyl carboxylate ethyl ester.

Experiment 4

Synthesis of 5,5-diphenylisoxazoline carboxylate ethyl ester

The cyclopropane derivative, 2,2-diphenylcyclopropanyl carboxylate ethyl ester (0.97 g, 3.7 mmol) was dissolved in 3.7 mL CF$_3$CO$_2$H. Into the solution was added NaNO$_2$ (0.28 g, 4.0 mmol, 1.1 eq.) in several ports so that the reaction temperature did not excess 40° C. After addition, the reactants were stirred at room temperature (about 18° C.) for half an hour. And the reactants were poured into an iced water and extracted with diethyl ether (2×20 mL); the ethereal solutions were combined and subsequently washed with sat. NaHCO$_3$ (2*20 mL), then water (20 mL) and brine (20 mL). The washed ethereal solution was then dried over anhydrous Na$_2$SO$_4$. After removing the desiccant, the ethereal solution was concentrated to obtain a light brown oil. The crude product $^1$H NMR of the crude product showed that the reaction was clean and a virtual 100% yield. The crude product was further purified over silica chromatography (Rf: 0.45, eluent: 20% ethyl acetate in petrol) to obtain 5,5-diphenylisoxazoline carboxylate ethyl ester 0.958 g (89% yield) as a white solid. $^1$H NMR (400 MHz, CDCl$_3$): 7.41-7.26 (10H, m), 4.34 (2H, q, J=7.1 Hz), 3.86 (2H, s), 1.36 (3H, t, J=7.1 Hz). $^{13}$C NMR (400 MHz, CDCl$_3$): 160.54, 151.09, 142.99, 128.54, 128.02, 125.95, 94.79, 62.15, 46.78, 14.12.

Example 5

Synthesis of 5,5-diphenylisoxazoline carboxylate ethyl ester

The cyclopropane derivative, 2,2-diphenylcyclopropanyl carboxylate ethyl ester (1.0 g, 3.8 mmol) was dissolved in 4.0 mL AcOH at room temperature (18° C.). Into the solution was carefully added 2.0 mL concentrated $H_2SO_4$, followed by adding $NaNO_2$ (0.29 g, 4.1 mmol, 1.1 eq) in several portions so that the reaction temperature did not excess 40° C. After addition, the reactants were stirred at room temperature (about 18° C.) for half an hour before the reactants were poured into iced water and extracted with diethyl ether (2×20 mL), the ethereal solutions were combined and washed with sat. $NaHCO_3$ (2×20 mL), then water (20 mL) and brine (20 mL). The washed ethereal solution was then dried over $Na_2SO_4$. After removing the desiccant, the ethereal solution was concentrated to furnish a thick oily product. The $^1H$ NMR of the crude product showed that the reaction was clean and the yield was virtually 100%. The thick oily crude product was stirred with 10 mL petrol to give a pale yellow solid 1.07 g, 97% yield.

Example 6

Synthesis of 5,5-diphenylisoxazoline carboxylate ethyl ester

The crude cyclopropane derivative, 2,2-diphenylcyclopropanyl carboxylate ethyl ester (generated through the reported one step procedure as a crude product in 107% yield) (1.14 g, 4.3 mmol) was dissolved in 4.0 mL AcOH at room temperature (18° C.). Into the solution was carefully added 2.0 mL concentrated $H_2SO_4$, followed by adding $NaNO_2$ (0.33 g, 4.7 mmol, 1.1 eq) in several portions so that the reaction temperature did not excess 40° C. After addition, the reactants were stirred at room temperature (about 18° C.) for half an hour. And the reactants were poured into an iced water and extracted with diethyl ether (2×20 mL), the ethereal solutions were combined and washed with sat. $NaHCO_3$ (2×20 mL), then water (20 mL) and brine (20 mL) in sequence. The washed ethereal solution was then dried over $Na_2SO_4$. After removing the desiccant, the ethereal solution was concentrated to furnish a thick oily crude product. The $^1H$ NMR of the crude product showed that the reaction was clean and a virtual 100% yield. The thick oily crude product was stirred with 10 mL petrol to give a pale yellow solid 1.15 g, 91% yield (97% over yield in two steps based on diphenyl ketone hydrazine).

Example 7

Synthesis of 5,5-diphenylisoxazoline carboxylate ethyl ester

The crude cyclopropane derivative, 2,2-diphenylcyclopropanyl carboxylate ethyl ester (generated through the reported one step procedure as a crude product in 107% yield) (21.3 g, 80 mmol) was dissolved in 80.0 mL AcOH at room temperature (18° C.). Into the solution was carefully added 40.0 mL concentrated $H_2SO_4$, followed by adding $NaNO_2$ (6.1 g, 88 mmol, 1.1 eq) in several portions so that the reaction temperature did not excess 40° C. After addition, the reactants were stirred at room temperature (about 18° C.) for half an hour. And the reactants were poured into an iced water and extracted with diethyl ether (2×200 mL), the ethereal solutions were combined and washed with sat. $NaHCO_3$ (2×100 mL), then water (100 mL) and brine (50 mL) in sequence. The washed ethereal solution was then dried over $Na_2SO_4$. After removing the desiccant, the ethereal solution was concentrated to furnish a thick oily crude product. The $^1H$ NMR of the crude product showed that the reaction was clean and a virtual 100% yield. The thick oily crude product was stirred with 10 mL petrol to give a pale yellow solid 21.7 g, 92% yield (98% over yield in two steps based on diphenyl ketone hydrazine).

What is claimed is:

1. A process for preparing isoxazoline derivatives represented by the general formula (1)

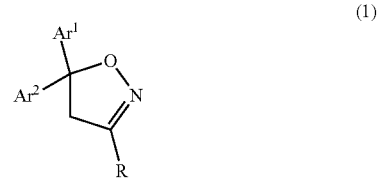

wherein $Ar^1$, $Ar^2$ represent aryl groups that may be substituted, and $Ar^2$ may or may not be the same as $Ar^1$; R represents an electron withdrawing group; characterized in that the isoxazoline derivatives represented by the general formula (1) are produced from the corresponding cyclopropane derivatives represented by the general formula (5)

wherein $Ar^1$, $Ar^2$ and R are as defined above, using the strategy of ring-opening and cyclization of the cyclopropane derivatives (5) with an electrophilic nitrosylation reagent at the temperature ranging from −20 to 100° C.

2. A process according to claim 1 wherein both $Ar^1$ and $Ar^2$ are phenyl groups, and R is ethoxycarbonyl group.

3. A process according to claim 1 wherein the cyclopropane derivative is ethyl 2,2-diphenylcyclopropanylcarboxylate.

4. A process according to claim 1 wherein the electrophilic nitrosylation regent is selected from the group consisting of nitrosylchloride, nitrosylbromide, nitrosylsulfonic acid; or the electrophilic nitrosylation regent is at least one member of nitrite salts selected from the group consisting or lithium nitrite, sodium nitrite, potassium nitrite combined with at least one member of strong acid selected from the group consisting of hydrogen chloride, hydrogen bromide, sulphuric acid, nitric acid, trifluoroacetic acid, boron trifluoride, boron trichloride, aluminium chloride.

5. A process according to claim 4 wherein the nitrosylation reagent is composed of sodium nitrite and sulphuric acid; the sulphuric acid is used in an amount of 3.0 moles to 30.0 moles per mole of sodium nitrite.

6. A process according to claim 1 wherein the cyclopropane derivative is used at a concentration of 0.1 moles per liter to 10.0 moles per liter.

7. A process according to claim 1 wherein the nitrosylation reagent is used in an amount of 1.0 mole to 10.0 moles for every one mole of the cyclopropane derivative used.

8. A process according to claim 7 wherein the nitrosylation reagent is used in an amount of approximately 1.1 moles per mole of the cyclopropane derivative.

9. A process according to claim 1 further comprises a solvent wherein the solvent is at least one member selected from hydrocarbons, chlorinated hydrocarbons, aromatic hydrocarbons, esters, ethers, halogenated aromatic hydrocarbons, acetonitrile, acetic acid, trifluoroacetic acid.

10. A process according to claim 9 wherein the solvent is acetic acid.

11. A process according to claim 1 wherein the reaction temperature is within the range of 0° C. to 40° C.

* * * * *